US006364859B1

(12) United States Patent
St. Romain et al.

(10) Patent No.: US 6,364,859 B1
(45) Date of Patent: Apr. 2, 2002

(54) LOCKING CAP FOR REPLACEABLE NEEDLE ASSEMBLY

(75) Inventors: Kenny J. St. Romain, Plaquemine, LA (US); Paul B. Robbins, Palo Alto; David J. Wright, Fremont, both of CA (US)

(73) Assignee: Robbins Scientific Corporation, Sunnyvale, CA (US)

( * ) Notice: Subject to any disclaimer, the term of this patent is extended or adjusted under 35 U.S.C. 154(b) by 0 days.

(21) Appl. No.: 09/586,246

(22) Filed: May 31, 2000

Related U.S. Application Data

(63) Continuation-in-part of application No. 09/324,570, filed on Jun. 2, 1999, now abandoned.
(60) Provisional application No. 60/089,422, filed on Jun. 16, 1998.

(51) Int. Cl.[7] .............................................. A61M 5/315
(52) U.S. Cl. ....................................................... 604/218
(58) Field of Search ................................ 604/218, 187, 604/110, 227, 214, 264, 107, 199, 221, 220, 224

(56) References Cited

U.S. PATENT DOCUMENTS

| | | | |
|---|---|---|---|
| 3,608,539 A | 9/1971 | Miller | 128/2 |
| 3,921,864 A | 11/1975 | Dawes | 222/386 |
| 4,013,080 A | 3/1977 | Froning | 128/347 |
| 4,926,860 A | 5/1990 | Stice et al. | 606/144 |
| 5,496,278 A | 3/1996 | Buff | 604/110 |

FOREIGN PATENT DOCUMENTS

| | | |
|---|---|---|
| WO | 95/17916 | 7/1995 |

*Primary Examiner*—Manuel Mendez
(74) *Attorney, Agent, or Firm*—Oppenheimer Wolff & Donnelly LLP; Larry B. Guernsey

(57) ABSTRACT

A syringe with replaceable needle assembly (10), having a syringe barrel (18) with a proximal end (14), a distal end (16), and an outer surface (87). The syringe barrel (18) surrounds an internal bore (20). A plunger assembly (60) is inserted into the syringe barrel internal bore (20). A needle assembly (80) has a sealing portion (72), which is configured to be removably insertable into the internal bore (20). The sealing portion (72) forms a fluid-tight seal with the internal bore (20). The needle assembly (80) further includes a releasable locking mechanism (79), which includes a collar (76) having a locking flange (86). Also disclosed is a replaceable needle assembly (80), which releasably locks onto the outer surface (87) of the proximal end (14) of a syringe barrel (18). The replaceable needle assembly (80) includes a collar (76), having a locking flange (86), which engages the outer surface (87) of the syringe barrel (18), and releasably locks the replaceable needle assembly (80) onto the syringe barrel (18).

20 Claims, 4 Drawing Sheets

LOCKING CAP FOR REPLACEABLE NEEDLE ASSEMBLY

The following is a continuation-in-part of application Ser. No. 09/324,570 filed on Jun. 2, 1999, now abandoned, which in turn claims priority from U.S. Provisional Application Ser. No. 60/089,422, filed Jun. 16, 1998.

TECHNICAL FIELD

The present invention relates generally to dispensing devices used in laboratory analysis and more particularly to syringes for dispensing liquid for use in medical and chemical analysis.

BACKGROUND ART

Syringes are commonly used in laboratories for dispensing precise quantities of materials. The hollow narrow gauge needles used at the syringe tips allow very exact measurement and delicate placement of materials. This same delicacy of mechanism means that the needles used can be easily damaged by chance collisions with other objects or clogged by inconsistencies in the material to be dispensed. When such needles are damaged, they must routinely be replaced.

Prior art needles are commonly glued into the glass barrel of the syringe, in which case the entire syringe must be discarded, or reworked by heating the syringe until the needle is released from the barrel. A new needle can be then be inserted and glued into place. This reworking operation can be less expensive than buying a new syringe, but requires that the damaged pieces be collected, packaged and returned to the manufacturer.

Alternatively, some prior art syringes are made with removable needles. However, these syringes usually require that a collar with machined threads be glued to the syringe barrel. The needle is usually attached to a Teflon™ pad which seats against the end of the barrel at the zero line. A cap with a central aperture is then inserted over the needle, and the cap, which is typically fitted with a threaded portion, engages the threads on the collar to hold the needle securely in place. This has the advantage of allowing easy replacement of the needle, but is more expensive from a manufacturing standpoint, since extra components such as the collar and cap must be produced and provided with machined threads and physically attached to the syringe.

Another problem with a screw-on collar is that if the collar is not tightened enough, the syringe may leak at the join. At the other extreme, if too much torque is applied in an effort to prevent leaks, the glue seal between the glass and the collar can break, thus causing damage to the device and causing additional leaks.

Thus there is a need for a syringe with a replaceable needle which can be assembled to produce a liquid-tight seal without the use of costly attachment mechanisms found in the prior art.

DISCLOSURE OF INVENTION

Accordingly, it is an object of the present invention to provide a syringe with a replaceable needle, which is less prone to damage during replacement.

Another object of the present invention is to provide a syringe with a replaceable needle with a simplified joining mechanism.

A further object of the present invention is to provide a syringe with a replaceable needle which is not glued to the syringe barrel.

A still further object of the present invention is to provide a syringe with replaceable needle which does not require machining of threads on the mating parts and is thus easy to manufacture and less expensive.

An additional object of the present invention is that a flexible, two-stage needle can be used as the replaceable needle.

Briefly, one preferred embodiment of the present invention is a syringe with replaceable needle assembly, having a syringe barrel with a proximal end, a distal end, and an outer surface. The syringe barrel surrounds an internal bore having an internal diameter. A plunger assembly is inserted into the syringe barrel internal bore. A needle assembly has a sealing portion which is configured to be removably insertable into the internal bore. The sealing portion forms a fluid-tight seal with the internal bore. The needle assembly further includes a releasable locking mechanism which includes a collar having a locking flange.

A second preferred embodiment is a replaceable needle assembly, which releasably locks onto the outer surface of the proximal end of a syringe barrel. The replaceable needle assembly includes a collar, having a locking flange, which engages the outer surface of the syringe barrel, and releasably locks the replaceable needle assembly onto the syringe barrel.

An advantage of the present invention is that the needle is quickly and easily replaced without damage to the needle or the barrel of the syringe.

Another advantage of the present invention is that no glue or adhesive is required to join the parts.

A further advantage of the present invention is that no screw threads are used to join the parts, thus the device is easy and inexpensive to manufacture.

An additional advantage of the present invention is that a two-stage needle can be used in which a very narrow gauge tip portion is partially enclosed with a rigid portion which allows for less damage to the tip, while maintaining enough rigidity for precise guidance.

BRIEF DESCRIPTION OF THE DRAWINGS

The purposes and advantages of the present invention will be apparent from the following detailed description in conjunction with the appended drawings in which.

BEST MODE FOR CARRYING OUT THE INVENTION

Figure 1:
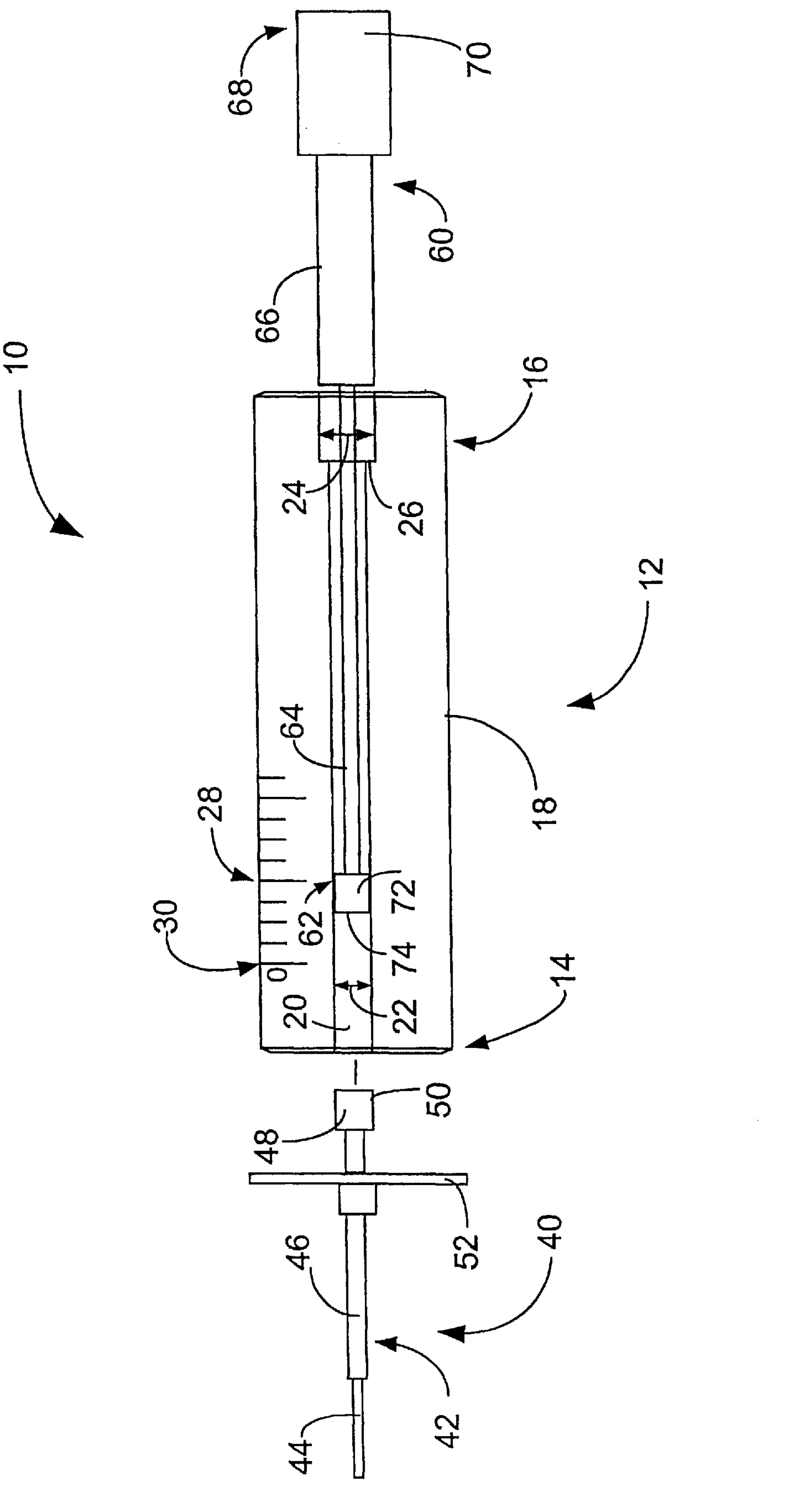
FIG. 1 shows a side view of a syringe having a replaceable needle assembly of the present invention which has been expanded in a vertical direction to illustrate the features more clearly.

A preferred embodiment of the present invention is a syringe having a replaceable needle assembly. As illustrated in FIG. 1, the general reference character 10 depicts a form of this preferred embodiment of the inventive device.

The present invention 10 uses a needle that is fitted with a sealing portion which fits into the syringe barrel proximate end. This sealing portion is covered with a film of sealing material, in this case Teflon™, which acts to form a liquid-tight seal with the syringe barrel.

The present invention 10 can be used either singly or in syringe arrays as are disclosed in co-pending application Ser. No. 60/119,470, which has been assigned to the assignee of the present application.

FIG. 1 illustrates a syringe with replaceable needle assembly 10. The figure has been expanded greatly in a vertical direction to illustrate more clearly the features of the invention. A syringe 12 has a proximal end 14, a distal end 16, and a barrel 18 containing an internal bore 20 having a small bore diameter 22. A section of the bore 20 near the distal end 16 has an enlarged internal diameter portion 24, forming a bore shoulder 26 where the enlarged diameter portion 24 reduces to the small bore diameter 22. The barrel also contains a number of volumetric markings 28 increasing from a zero mark 30.

A needle assembly 40 includes a needle 42 which itself includes a hollow inner member 44 of very small diameter, a sheath portion 46 and a sealing portion 48. The sheath portion 46 serves to protect and provide structural support and rigidity for the inner member 44. The sealing portion 48 is inserted into the proximal end 14 of the bore 20 of the barrel 18. The tip of the sealing portion 46 is coated with a film of sealing material 50, in this case Teflon™, which acts to form a liquid-tight seal with the bore 20 of the syringe barrel 18. The needle assembly 40 also includes a hub 52 which serves to protect the proximal end 14 of the barrel 18, and adds further structural support to the needle 42 against lateral bending. The hub 52 is glued to the needle 42, and provides a convenient grip for removing the entire needle assembly 40 whenever replacement is necessary. The hub 52 also provides a stop for travel of the needle 42 insertion into the bore 20, so that the tip of the sealing portion 48 is correctly aligned with the zero mark 30.

The syringe 12 also includes a plunger 60 with a proximal end 62, a shaft 64, an enlarged shaft portion 66 and a distal end 68 with a handle 70. The proximal end 62 also includes a sealing portion 72, also coated with a film of sealing material 74, in this case also Teflon™, which forms a liquid-tight seal with the bore 20 of the syringe barrel 18. The combined length of the shaft 64 and the sealing portion 72 are carefully designed to match the portion of the length of the bore 20 having the smaller bore diameter 22 as measured in the distal direction from the zero mark 30. The enlarged shaft portion 66 is designed to fit within the enlarged diameter bore portion 24, but will be stopped at the bore shoulder 26 when the portion having the smaller bore diameter 22 is reached. The needle assembly 40 is inserted into the proximal end 14 so that the end of the sealing portion 48 is aligned with the zero mark 30 when the hub 52 abuts the proximal end 14 of the barrel 18. The bore shoulder 26 thus prevents the plunger 60 from travelling so far toward the proximal end 14 of the bore 20 that the needle assembly 40 is pushed out of the bore 20 or moved out of alignment with the zero mark 30.

Since the sealing portion 48 of the needle assembly 40 is held in place by a friction fit with the internal bore 20, the needle assembly is easily removed when replacement is necessary. The hub 52 is grasped and pulled until the sealing portion 48 is released from the proximal end 14 of the barrel 18 and a new needle assembly 40 is then quickly and conveniently installed. The simplified design allows for greatly reduced production costs, requiring fewer parts, less complex machining of the parts that are used and faster replacement of needles.

Figure 2:
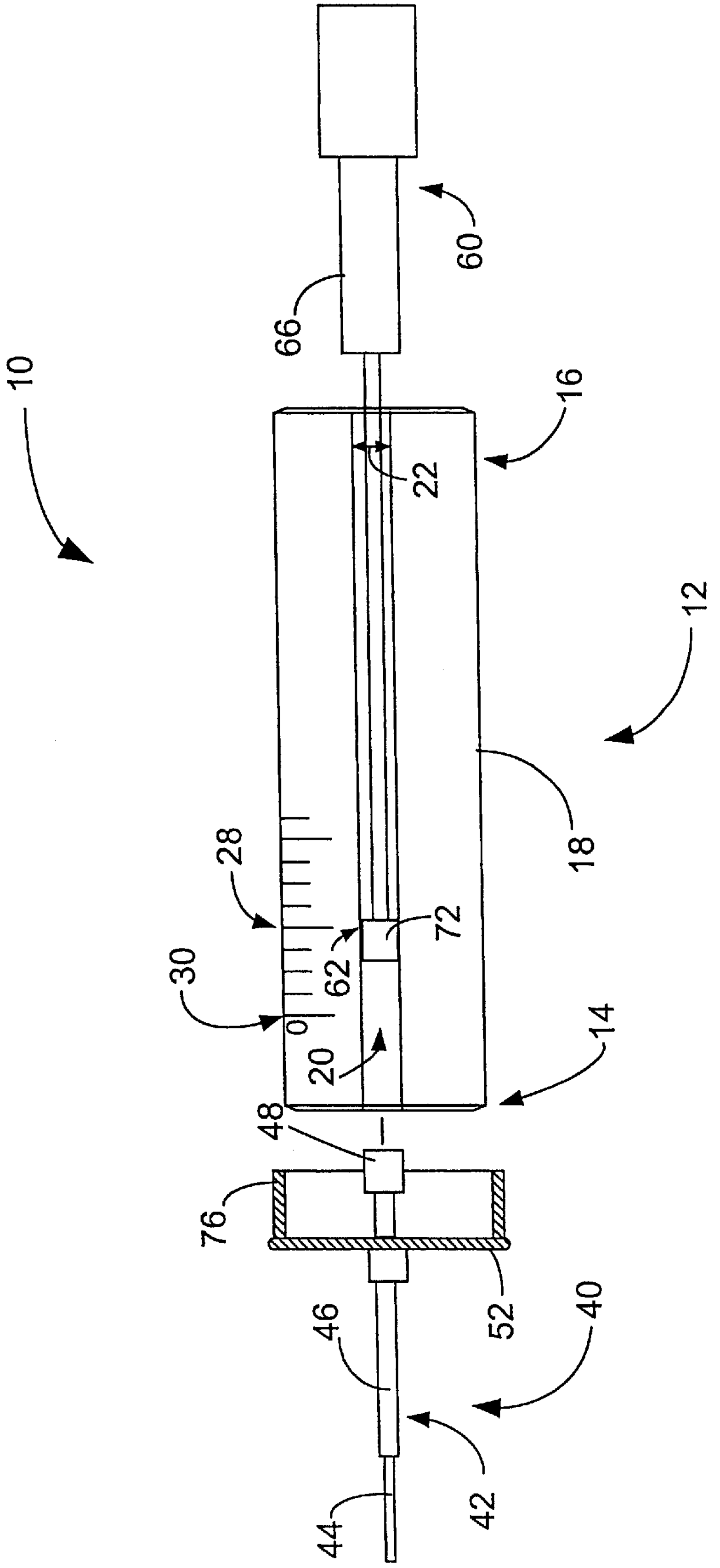
FIG. 2 shows a side view of an alternate embodiment of a syringe having a replaceable needle assembly which has also been expanded in a vertical direction to illustrate the features more clearly.

An alternate embodiment, which is currently most preferred, is shown in FIG. 2. In this embodiment, the hub 52 has been fitted with an additional collar 76 with fits over the proximal end 14 of the barrel 18. The needle assembly 40 is held in place by the engagement of the sealing portion 48 with the internal bore 20 as before, but the collar 76 adds additional lateral support and acts to protect the needle 42 from damage.

Additionally, the enlarged internal diameter portion (24 in FIG. 1) has been eliminated. The inner bore 20 is now of a constant diameter 22 throughout the syringe length. In order to stop the advancement of the plunger 60 at the appropriate distance, a portion of the shaft 66 has again been enlarged so that forward motion is stopped when it reaches the smaller diameter 22 of the bore 20. This ensures that the plunger proximal end 62 aligns with the zero mark 30, as before. There is optionally a slight funnel shaped enlargement of the internal bore 20 at either or both ends 14, 16 which can help to guide the sealing portions 72, 48 of the plunger 60 and the needle assembly 40 into the inner bore 20 when the syringe 12 is being assembled.

The inner member 44 of the needle 42 in this embodiment is of highly flexible material such as super elastic nitinol alloy BB, (binary nickel-titanium alloy) currently available from Memry Corporation. This high flexibility allows the needle inner member 44 to bend easily to 90 degrees or more and elastically return to its original angle without breaking. The sheath portion 46 protects the inner member 44 from damage, and allows the needle tip to be guided with more precision and direction. The inventors have found this “two-stage” needle design to be particularly useful by providing an excellent combination of flexibility in the first stage and rigidity in the second stage which is very helpful in performing very precise operations in small dimensioned spaces. The present applicants are not aware of any such a two stage assembly 47 having such a highly flexible inner member, and assert this as an independently novel feature.

Figure 3:
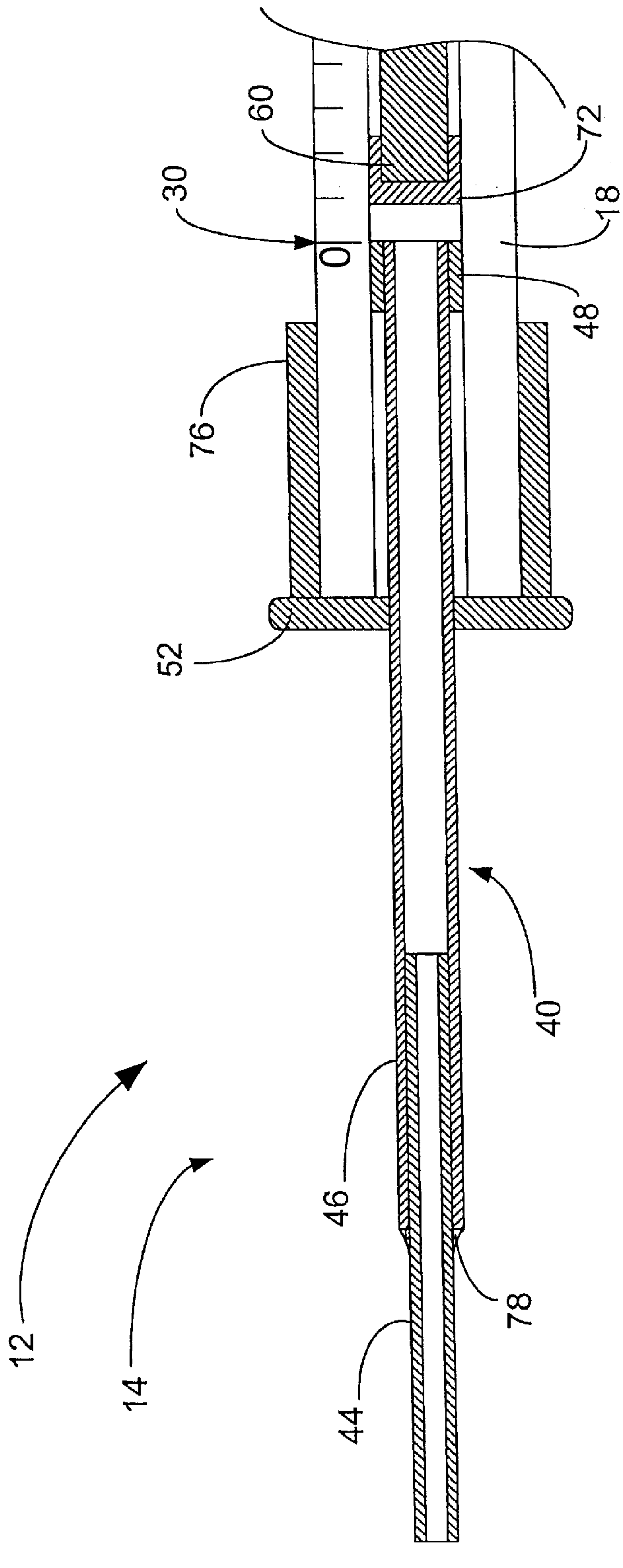
FIG. 3 illustrates a detailed cutaway side view of the replaceable needle assembly and barrel of the syringe.

FIG. 3 shows a close-up detail view of the proximal end 14 of a syringe 12, showing the needle assembly 40 in place upon the barrel 18. The hub 52 and collar 76 are shown in engagement with the barrel 18. The needle sealing portion 48 is shown seated at the zero mark 30. The plunger 60 has been withdrawn slightly so that the plunger sealing portion 72 is drawn back from the zero mark 30. Inner member 44, made of flexible material, is shown installed in outer sheath 46. A seal 78 has been fashioned at the end of the outer sheath 46 and upon the inner member to prevent external material from entering the needle and contaminating the contents.

Of course, it is possible to practice the present invention without using a two-stage needle, or by using a first stage made from material which is not super-elastic. It is possible also to use a collar 76 which may be made of or coated with sealing material such as Teflon to engage the barrel outer surface in the same manner that the needle sealing portion engages the internal bore. It is also possible that there be no such coating or material, and that the collar 76 be separated from the barrel 18 by a small distance, such that the collar does not touch the barrel, but still provides protection for the needle by limiting lateral and angular movement of the barrel 18 relative to the needle 40.

Figures 4, 5:
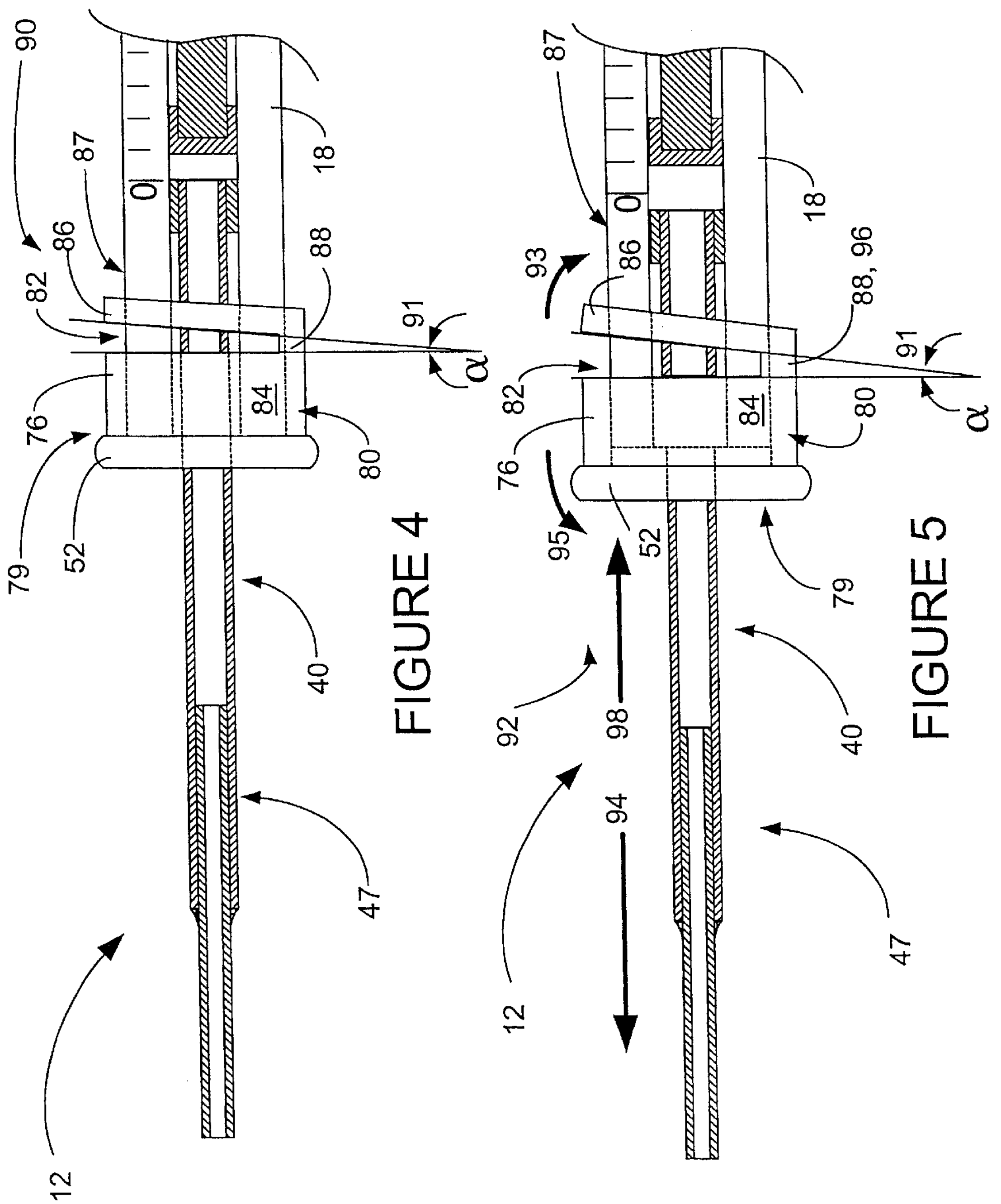
FIG. 4 shows a detailed cutaway side view with the locking needle assembly superimposed, the needle assembly being in a relaxed position.
FIG. 5 shows a detailed cutaway side view with the locking needle assembly superimposed, the needle assembly being in a locked position.

FIGS. 4 and 5 illustrate another embodiment, which has now become most preferred. The applicants have discovered that the needle assembly 40, which is held in place on the syringe barrel 18, is prone to being accidentally dislodged if the hub 52 is pulled upon, or catches on some external projection, or if there is blockage in the internal bore of the needle. If such a blockage develops, pressure can build in the needle assembly 40, which tends to push the entire assembly 40 from its engagement with the barrel 18. This can lead to spillage of the syringe contents, which is highly undesirable, since the contents can include toxins or biologically dangerous substances. It is desirable therefore to provide a locking which can be easily engaged and disengaged, but which provides a sturdy lock between the removable needle assembly 40 and the barrel 18.

FIG. 4 shows such a locking mechanism 79 which is simple and easy to use and to manufacture. The syringe 12 is shown having a needle assembly 40, in this case having a two stage needle 47, although this is optional. A locking cap assembly 80 is shown which is generally made from a hub 52 and collar 76, as before, except that the collar 76 includes a groove 82 which separate the collar 76 into a main portion 84 and a locking flange 86 which are joined at a hinge portion 88. The locking cap assembly 80 engages the outer surface 87 of the syringe barrel 18, which is shown fully inserted into the collar 76 in FIG. 4. The locking cap assembly 80 is assumed to be in relaxed position 90, wherein the locking flange 86 is positioned in a flange angle of 91 relative to the main portion 84, and the hinge portion 88 is not flexed. Although it is possible that the locking flange 86 be positioned substantially parallel to main portion 84, (thus $\alpha=0°$), it is preferred that the locking flange 86 be at a slight angle so that flange angle a 91 is in the range of 10° to 20°. It is also possible that locking flange 86 include engaging elements, a releasable sticky adhesive surface, or teeth (all not visible in figure) on the interior of the flange to increase the grip of the locking flange 86 on the barrel outer surface 87. This may also influence the desired flange angle α91.

FIG. 5 shows the syringe 12 with needle assembly 40 in which the locking cap assembly 80 is in locked position 92. When the needle assembly 40 is pulled in the proximal direction 94, or if internal pressure acts to push the needle assembly 40 off of the barrel 18, main portion 84 thus moves in the proximal direction 94. The locking flange 86 tends to remain engaged with the outer surface 87 of the barrel 18, causing it to pivot slightly about the hinge portion 88, which is thin enough to flex slightly, but rigid enough to also act as a spring element 96. This spring element 96 urges the main portion 84 to pull in the distal direction 98, and also to tend to rotate the locking flange 86 slightly in a first pivotal direction 93 so the flange angle α91 increases, in the case pictured, clockwise. The main portion 84 may be urged to rotate in a second pivotal direction 95, also frictionally engaging the outer surface 87 of the barrel 18, thus aiding in locking the needle assembly 40 onto the barrel 18.

To disengage the locking flange 88 and allow the needle assembly 40 to be removed, the user merely needs to push the locking flange 86 and the whole locking cap assembly 80 in the proximal direction. The locking flange 86 may flex slightly in the proximal direction 94, but is prevented from flexing so much as to engage the barrel 18 by running into the main portion 84. Thus the needle assembly 40 can be pushed off by proper external manipulation, but not by pulling, or by internal pressure.

In addition to the above mentioned examples, various other modifications and alterations of the inventive syringe with replaceable needle assembly 10 may be made without departing from the invention.

INDUSTRIAL APPLICABILITY

The syringe with replaceable needle assembly 10 is well suited for application in any laboratory situation in which very precise quantities of liquids are to be dispensed or distributed. Especially in situations where high volumes of chemical processing take place or where many repetitions of material dispensing are done, the present invention will be a welcome improvement.

Very small gauge needles are often used in conjunction with sequencing gels which are used in automatic sequencers. The sequencing gels are typically sandwiched between two glass plates. These sequencing gels are typically 0.2 mm or 0.4 mm thick, so very small gauge needles are required. Since the needles are naturally hollow to allow for material flow, the wall thickness of these needles is thus very small indeed. It is understandable then, that in trying to guide needles of such very thin wall thickness into the opening between two hard surfaces spaced so a closely together, the needles are very prone to damage. These difficulties are of course compounded when the needle placement is done in a high repetition setting. In these situations, wear and tear on needles often requires that damaged needles be replaced with new needle assemblies, if possible, or with completely new syringes with new needles permanently attached, if replaceable needle assemblies are not available.

The present invention 10 makes processing more efficient in two ways. First, by using two-stage needles, with the second stage 44 made of such highly flexible material as binary nickel-titanium alloy, damage to the needle tip is minimized, so that replacements are necessary less often. By having a sheath 46 of rigid material, and an inner member 44 of highly flexible material, enough rigidity is provided that the needle 42 can be easily guided to the desired position, but by having a flexible tip, the most narrow gage portion is made less fragile.

Even with a highly flexible inner member, in high repetition situations the needle will still need replacement periodically. The second way that the present invention improves efficiency is that replacement of the needle assembly 40 can be very quickly and easily accomplished. The hub 52 or collar 76 can be grasped by fingers and the needle assembly 40 pulled from the syringe barrel 18 and a new needle assembly 40 installed in a matter of seconds, without the use of tools. By reusing the barrel 18 and plunger portions 60, which are generally undamaged, there is less waste and less cost involved than replacing the entire syringe assembly.

Prior art replaceable needle syringes typically used a steel collar which was permanently glued to the syringe barrel. This collar would have screw-on threads machined onto it, and the needle assembly would have mating threads. By eliminating screw threads and making the collar 76 of the same piece as the hub 52, the manufacturing cost of the present invention 10 are greatly reduced. In addition, there is no chance of cross-threading the mating parts, or of tightening them too much and damaging the syringe, the mating parts or the glue join between the collar and the barrel, or tightening too little and allowing material to leak.

The syringe with replaceable needle assembly 10 is also particularly useful in syringe arrays, such as is described in currently pending application Ser. No. 60/119,470, which has been assigned to the assignee of the present application. In a syringe array, it is particularly efficient to be able to replace needle assemblies without disassembling the array to replace an entire syringe. Also, when multiple syringes are used, there are naturally more needles in play during a process step, and more opportunity for damage to one or more needles. Thus it is very efficient to be able to be able to quickly and easily replace needles as required.

For the above, and other, reasons, it is expected that the syringe with replaceable needle assembly 10 of the present invention will have widespread industrial applicability. Therefore, it is expected that the commercial utility of the present invention will be extensive and long lasting.

What is claimed is:

1. A syringe with replaceable needle assembly, comprising:

a syringe barrel having a proximal end, a distal end, and an outer surface, said syringe barrel surrounding an internal bore, said bore having an internal diameter;

a plunger assembly, which is inserted into said syringe barrel internal bore; and a needle assembly having a sealing portion, said sealing portion being configured to be removably insertable into said internal bore, said sealing portion forming a fluid-tight seal with said internal bore, said needle assembly further having a releasable locking mechanism which includes a collar having a locking flange.

2. A syringe with replaceable needle assembly as in claim 1, wherein:

said collar includes a main portion and said locking flange; and said locking flange is attached to said main portion by a hinge portion.

3. A syringe with replaceable needle assembly as in claim 1, wherein:

said locking flange engages said outer surface of said syringe barrel, such that movement of said needle assembly in a proximal direction relative to said syringe barrel is prevented unless said locking flange is disengaged from said outer surface of said barrel.

4. A syringe with replaceable needle assembly as in claim 3, wherein:

said locking flange is disengaged by applying force upon said locking flange to urge it in a proximal direction.

5. A syringe with replaceable needle assembly as in claim 4, wherein:

said locking flange and said main portion are positioned to lie at a flange angle with respect to each other.

6. A syringe with replaceable needle assembly as in claim 5, wherein:

said flange angle is chosen to lie in the range of 10° to 20°.

7. A replaceable needle assembly, which locks onto the outer surface of the proximal end of a syringe barrel, comprising:

a collar, which includes a main portion and a locking flange, said locking flange being connected to said main portion by a hinge portion, said locking flange engaging which engages said outer surface of said syringe barrel, and releasably locks is said replaceable needle assembly onto said syringe barrel.

8. A replaceable needle assembly as in claim 7, wherein:

said collar includes a main portion and said locking flange; and said locking flange is attached to said main portion by a hinge portion.

9. A replaceable needle assembly as in claim 7, wherein:

said locking flange engages said outer surface of said syringe barrel, such that movement of said needle assembly in a proximal direction relative to said syringe barrel is prevented unless said locking flange is disengaged from said outer surface of said barrel.

10. A replaceable needle assembly as in claim 9, wherein:

said locking flange is disengaged by applying force upon said locking flange to urge it in a proximal direction.

11. A replaceable needle assembly as in claim 10, wherein:

said locking flange and said main portion are positioned to lie at a flange angle with respect to each other.

12. A replaceable needle assembly as in claim 11, wherein:

said flange angle is chosen to lie in the range of 10° to 20°.

13. A replaceable needle assembly as in claim 7, wherein:

said locking flange includes teeth which engage said outer surface of said barrel.

14. A replaceable needle assembly as in claim 7, wherein:

said locking flange includes a releasably sticky adhesive surface which engages said outer surface of said barrel.

15. A replaceable needle assembly, which locks onto the outer surface of the proximal end of a syringe barrel, comprising:

a collar including a groove which divides said collar into a main portion and a locking flange which are connected at a hinge portion, so that when said collar is pulled upon, said locking flange pivots in a first pivotal direction about said hinge portion and engages said barrel outer surface thus locking said collar in place.

16. A replaceable needle assembly as in claim 15, wherein:

said locking flange is disengaged by applying force upon said locking flange to urge it to pivot about said hinge portion in a direction counter to said first pivotal direction, thus releasing said locking flange from engagement with said barrel outer surface.

17. A replaceable needle assembly as in claim 15, wherein:

said locking flange and said main portion are positioned to lie at a flange angle with respect to each other.

18. A replaceable needle assembly as in claim 17, wherein:

said flange angle is chosen to lie in the range of 10° to 20°.

19. A replaceable needle assembly as in claim 15, wherein:

said locking flange includes teeth which engage said outer surface of said barrel.

20. A replaceable needle assembly as in claim 15, wherein:

said locking flange includes a releasably sticky adhesive surface which engages said outer surface of said barrel.

* * * * *